Figure 1:
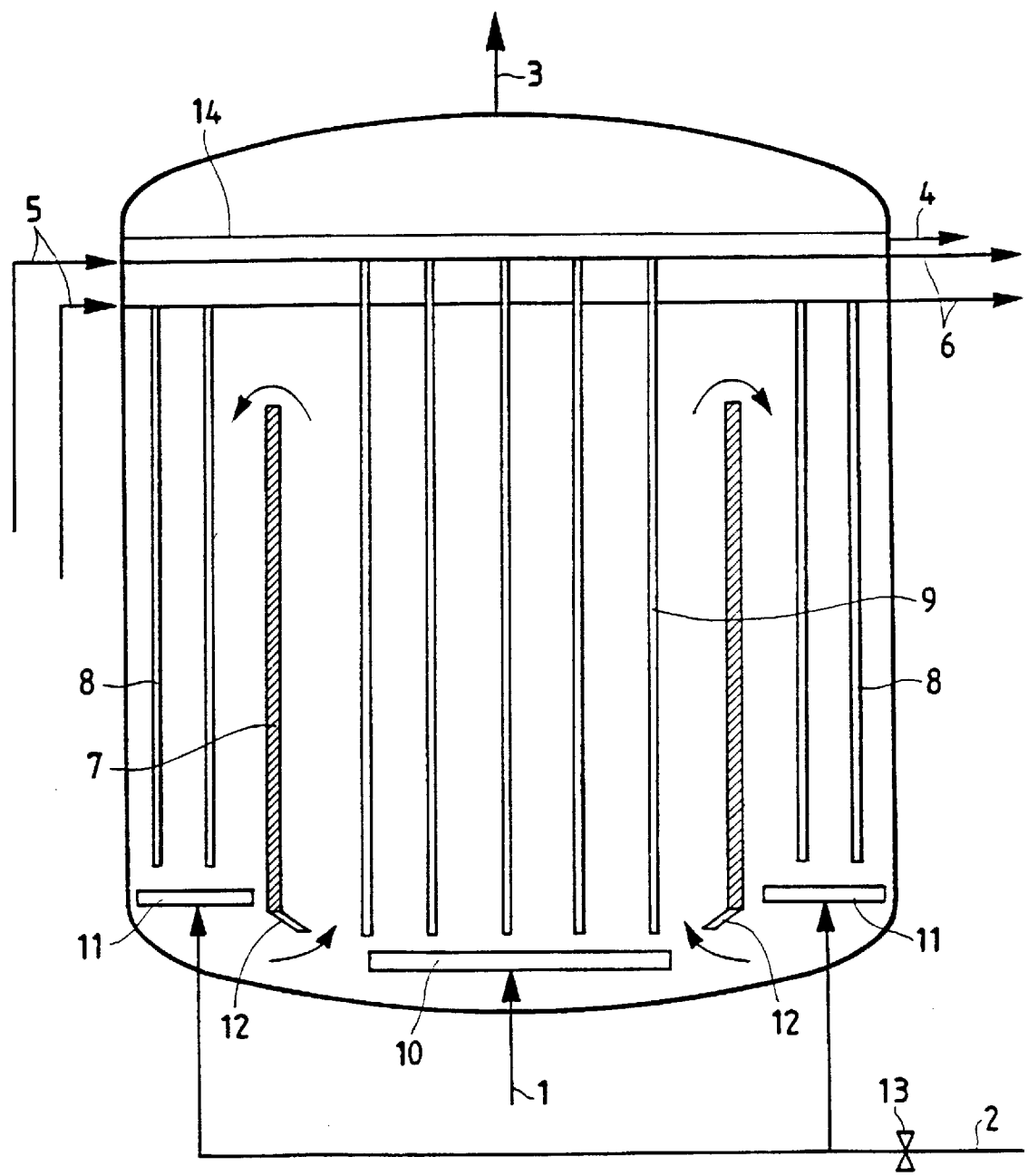

United States Patent [19]
Maretto et al.

[11] Patent Number: 6,162,754
[45] Date of Patent: Dec. 19, 2000

[54] PROCESS FOR REGENERATING A CATALYST CONTAINED WITHIN A BUBBLE-COLUMN REACTOR WITH DRAFT-TUBE AND PROCESS FOR THE PRODUCTION OF A HYDROCARBON

[75] Inventors: Cristina Maretto, Padova; Vincenzo Piccolo, Milan, both of Italy; Dominique Casanave, Villeurbanne; Pierre Galtier, Vienne, both of France

[73] Assignees: Agip Petroli S.p.A.; ENI S.p.A., both of Rome, Italy; Institut Francais du Petrole, Rueil-Malmaison, France

[21] Appl. No.: 09/147,736
[22] PCT Filed: Jun. 20, 1998
[86] PCT No.: PCT/EP98/03874
§ 371 Date: Mar. 18, 1999
§ 102(e) Date: Mar. 18, 1999
[87] PCT Pub. No.: WO99/00191
PCT Pub. Date: Jan. 7, 1999

[30] Foreign Application Priority Data
Jun. 26, 1997 [IT] Italy .................. MI97A1509

[51] Int. Cl.⁷ ................ B01J 20/34; B01J 38/56
[52] U.S. Cl. ............... 502/31; 502/30; 502/53; 518/700; 518/706; 518/709
[58] Field of Search .................. 502/30, 31, 53; 518/700, 706, 709

[56] References Cited

U.S. PATENT DOCUMENTS

| | | |
|---|---|---|
| 3,754,993 | 8/1973 | Oguchi et al. . |
| 5,252,613 | 10/1993 | Chang et al. .................. 518/700 |
| 5,268,344 | 12/1993 | Pedrick et al. .................. 502/30 |
| 5,288,673 | 2/1994 | Behrmann et al. .................. 502/30 |
| 5,827,902 | 10/1998 | Maretto et al. . |

FOREIGN PATENT DOCUMENTS 0325 337   7/1989   European Pat. Off. .

*Primary Examiner*—Steven P. Griffin
*Assistant Examiner*—Christina Ildebrando
*Attorney, Agent, or Firm*—Oblon, Spivak, McClelland, Maier & Neustadt, P.C.

[57] ABSTRACT

Continuous process for the production of prevalently heavy hydrocarbons starting from synthesis gas in the presence of a gas phase, a liquid and a solid catalyst, the above process being carried out using a bubble column, characterized in that the bubble column internally has: (a) at least one draft-tube; (b) at least one device for the inlet of the synthesis gas; (c) at least one device for the inlet of the regenerating gas; (d) at least one device for activating/interrupting the stream of regenerating gas; (e) optional devices suitable for minimizing the mixing of the synthesis gas with the regenerating gas.

14 Claims, 1 Drawing Sheet

PROCESS FOR REGENERATING A CATALYST CONTAINED WITHIN A BUBBLE-COLUMN REACTOR WITH DRAFT-TUBE AND PROCESS FOR THE PRODUCTION OF A HYDROCARBON

The present invention relates to a bubble-column reactor equipped with a draft-tube which can be used in triphase slurry processes, more specifically in the Fischer-Tropsch process.

The present invention also relates to a regeneration process of catalysts partially and reversibly deactivated, which uses the above reactor.

Slurry catalytic processes, i.e. operating in triphase systems essentially consisting of a gas phase and a liquid phase in which the solid catalyst is dispersed, particularly the Fischer-Tropsch process, have the disadvantage of a more or less distinct reversible deactivation of the initial catalytic activity of the catalyst. This drawback is generally resolved by the regeneration of the exhausted catalyst.

EP-A-590,882 describes a method for regenerating a catalyst for the synthesis of hydrocarbons, containing Cobalt or Ruthenium, subject to partial, reversible deactivation in a slurry synthesis process. This process enables a recovery of at least 80% of the initial activity of the catalyst.

The above method involves carrying out the regeneration of the catalyst in-situ of the slurry reactor, by periodically stopping the flow-rate of the process gas (synthesis gas) and sending a flow of gas containing hydrogen and other inert gases, avoiding the presence of components, such as for example carbon monoxide, capable of reacting with the hydrogen.

The process described in EP-A-590,882 has the disadvantage however of requiring a periodical interruption of the synthesis of hydrocarbons to substitute the process gas with the gas containing hydrogen.

U.S. Pat. No. 5,268,344 solves the problem by using a bubble column and carrying out the regeneration of the catalyst inside one or more draft-tubes situated inside the bubble-column reactor, the fraction of the column section occupied by the draft-tubes being preferably less than 10%. Unlike what is described in EP-A-590,882, this solution does not involve the interruption of the synthesis gas.

It is also known that in the field of reactions in triphase systems, bubble-column reactors equipped with a draft-tube are preferable to simple bubble-column reactors with respect to the distribution of the solid phase in the triphase system.

A particular bubble-column configuration equipped with a draft-tube has now been found which overcomes the above disadvantages.

In fact, the use of this particular bubble-column configuration enables the regeneration of the partially deactivated catalyst to be carried out in-situ (more specifically at the interspace between reactor and draft-tube), thus avoiding the periodical interruption of the feeding of the process gas.

In addition, the reactor of the present invention allows a better homogenization of the phases with respect to the bubble-column reactors used in the U.S. Pat. No. 5,268,344.

In accordance with this, the present invention relates to a continuous process for the production of prevalently heavy hydrocarbons, alternative fuels, octane enhancers, chemicals and chemical intermediates starting from synthesis gas in the presence of a gas phase, a liquid and a solid catalyst, the above process being carried out using a bubble column equipped with cooling devices and comprising the periodical internal regeneration of the reversibly, partially deactivated catalyst, said regeneration being carried out in the presence of a regenerating gas, characterized in that the bubble column internally has:

(a) at least one draft-tube, consisting of a substantially vertical cylinder, having smaller dimensions than the column, preferably positioned co-axially with respect to the column, with both the lower and upper ends open, completely immersed in the liquid phase containing the solid in suspension;

(b) at least one device for the inlet of the synthesis gas, preferably a gas distributor, preferably situated at the bottom of the bubble-column;

(c) at least one device for the inlet of the regenerating gas, preferably a gas distributor, preferably situated at the bottom of the interspace between the draft-tube and the internal wall of the reactor;

(d) at least one device which activates/interrupts the stream of regenerating gas;

(e) optional devices suitable for minimizing the mixing of the synthesis gas with the regenerating gas, preferably deflectors, preferably assembled near the lower opening of the draft-tube.

The term "regenerating gas" means the gas, usually hydrogen possibly diluted with inert gases, used for the rejuvenation—regeneration of the reversibly deactivated solid catalyst, preferably containing at least one metal of Group VIII, preferably selected from cobalt and iron, preferably cobalt.

The configuration of the bubble-column reactor of the present invention enables the catalyst to be regenerated without interrupting the reagent gases stream.

FIG. 1 represents a non-limiting example of the embodiment of the present invention. In order, the numbers refer to:
1—feeding line of the synthesis gas,
2—feeding line of the regenerating gas for the regeneration of the catalyst,
3—discharge line of the gas products (prevalently light hydrocarbons) and non-reacted components,
4—discharge line of the liquid products,
5—feeding line of the cooling fluid,
6—discharge line of the cooling fluid,
7—draft-tube,
8—cooling devices situated in the interspace between the draft and reactor,
9—cooling devices situated inside the draft-tube,
10—device for the inlet of the synthesis gas,
11—device for the inlet of the regenerating gas,
12—deflectors,
13—valve for activating/interrupting the stream of regenerating gas of the catalyst,
14—dispersion level (gas-liquid-solid).

In the diagram of FIG. 1 there are also arrows which indicate the direction of the movement of the internal circulation of the liquid, which is established by the draft-tube when the stream of gas containing hydrogen is interrupted.

In compliance with what is described in FIG. 1, the bubble column reactor of the present invention comprises internally a draft-tube (7), substantially vertical, which uses the process gas as carrier. This device is basically a vertical cylinder, with smaller dimensions than the bubble-column reactor, which is co-axially introduced inside the column, open at both ends and completely immersed in the liquid containing the solid in suspension. This allows the liquid and solid in suspension to circulate through the cylindrical device and interspace outside the cylinder, if the driving force due to the process gas entering the bottom of the column overcomes the pressure drops. The dimensions of this device (7) must be such that the lower end is preferably just above the bottom of the reactor, whereas the upper end is just below the free surface of the solid-liquid suspension containing the gas.

The synthesis gas, comprising carbon monoxide and hydrogen, is introduced into the bottom of the reactor by means of an appropriate device, preferably a distributor (10). The geometry of the distributor and the distance of the draft-tube from the bottom of the column are adequately selected to allow the process gas to flow inside the cylindrical device, thus avoiding preferential routes in the interspace zone. The Fischer-Tropsch synthesis reaction takes place inside the cylindrical device.

The regeneration of the catalyst is carried out with regenerating gas, preferably hydrogen, at high temperatures and pressures, corresponding to those adopted for the Fischer-Tropsch synthesis. The hydrogen is fed as a gas stream; this stream can contain inert gases, such as methane or other light hydrocarbons ($C_2$–$C_{10}$). It is preferable for them not to contain carbon monoxide or other components which can react with the hydrogen at the operating temperature and pressure of the Fischer-Tropsch synthesis.

As mentioned above, the above configuration of the bubble column allows the deactivated catalyst to be regenerated in-situ.

A further object of the present invention relates to a process for the regeneration in-situ of reversibly partially deactivated solid catalysts, prevalently containing metals of group VIII, preferably selected from cobalt and iron, the above method comprising the use of a reactor as described in claim 1 and avoiding the interruption of the synthesis gas during the above regeneration, which comprises:

(i) a first regeneration phase of the catalyst, in which a regenerating gas containing hydrogen is flushed into the interspace between the reactor and draft-tube, preferably from the lower part of the above interspace, for a time which is sufficient to regenerate the quantity of exhausted catalyst suspended in the liquid contained in the interspace, the flow-rate of the gas containing hydrogen being such as to balance the hydrostatic head between the draft zone and that of the interspace;

(ii) a second phase in which the feeding of the gas containing hydrogen is interrupted and the circulation of the liquid containing the solid in suspension is re-established by means of the draft-tube; in this way the regenerated catalyst obtained in phase (i) is substituted with the exhausted catalyst still present inside the reactor;

(iii) repetition of phases (i) and (ii), preferably until the total regeneration of the catalyst contained in the column reactor.

The term "regeneration of the catalyst" means the recovery of at least 80% of the initial catalytic activity of the catalyst.

In step (i) it is preferable to minimize the circulation of the liquid-solid suspension and gas between the cylindrical device and the interspace; this is achieved by acting on the flow-rate of gas containing hydrogen flushed into the interspace to balance the hydrostatic head between the two regions.

Appropriately shaped deflectors can be installed in the lower opening of the draft-tube to minimize the mixing of the two gas streams, that of the process gas and that containing hydrogen for regeneration.

In step (ii) the feeding of the regenerating gas is interrupted and the circulation of the liquid containing the solid in suspension is re-established by means of the draft-tube and process gas, whose flow-rate basically remains unvaried, the latter depending exclusively on the operating and process conditions established.

As mentioned above, the regeneration of the catalyst takes place in the interspace between the column and the cylindrical device, using a regenerating gas, preferably introduced by means of suitable distributors, preferably situated at the lower opening of the annular interspace.

The establishment of a forced circulation of liquid containing the solid in suspension between the draft-tube and interspace allows a new charge of exhausted catalyst, suspended in the liquid prevalently consisting of the hydrocarbons produced by the synthesis process, to enter the interspace thus substituting the suspension containing the regenerated catalyst.

The "regenerated catalyst", owing to the circulation established by the draft-tube, leaves the interspace to enter the reaction zone (inside the draft-tube) from the opening at the bottom, whereas the charge of "exhausted catalyst" passes from the reaction zone to the interspace, where the regeneration takes place, through the upper opening.

When the volume of the interspace has been completely renewed, one regeneration cycle is completed and the stream of regenerating gas in the interspace is re-opened starting a new regeneration cycle.

During both phase (i) and phase (ii), the Fischer-Tropsch reaction takes place in continuous inside the cylindrical device, whose volume represents the reaction volume, where the process gas is flushed.

The regeneration cycle is started when the activity of the catalyst deteriorates over a certain level, for example 50%, and is stopped when the catalyst has recovered the desired catalytic activity, preferably after recovering at least 80%, even more preferably at least 90%, of the original catalytic activity.

When the regeneration cycle and renewal of the regenerated charge is not carried out in the reactor of the present invention, the column reactor operates with continuous internal circulation of the liquid containing the solid in suspension due to the draft-tube permanently installed inside the reactor.

As is known to experts in the field, the internal circulation promotes the distribution of the solid in the suspension with the liquid, which would otherwise only be achieved by means of the bubbles of gas entering near the bottom of the column, thus making the concentration profile of the catalyst more uniform.

Owing to the exothermicity of both the Fischer-Tropsch synthesis reaction and the regeneration process, in order to maintain control of the temperature and practically isothermal conditions, a suitable cooling system is introduced into both the reaction and regeneration sections, consisting for example of tube-bundles, coils or other types of heat exchange surfaces immersed in the suspension bulk (slurry). In the Fischer-Tropsch synthesis process the temperature control is fundamental in that the temperature directly affects the selectivity of the reaction; in addition, it is important to preserve the catalyst from undesired overheating which could damage it.

The internal regeneration of the catalyst preferably takes place under the same conditions of temperature and pressure as the Fischer-Tropsch synthesis reaction. In any case it is possible to independently regulate the temperature both inside the reaction zone and in the regeneration zone.

The conditions, particularly of temperature and pressure, for synthesis processes of hydrocarbons are generally well known. The temperatures can be between 150° C. and 380° C., preferably from 180° C. to 350° C., even more preferably from 190° C. to 300° C. The pressures are generally higher than about 0.5 MPa, preferably from 0.6 to 5 MPa, more preferably from 1 to 4 MPa.

In the preferred embodiment of the present invention, i.e. in the synthesis of hydrocarbons via reduction of CO, the solid particles at least partly consist of particles of a catalyst selected from those, well-known to experts in the field, normally used for catalyzing this reaction. Any catalyst for the Fischer-Tropsch synthesis, particularly those based on iron or cobalt, can be used in the process of the present invention. Catalysts based on cobalt are preferably used, in which the cobalt is present in a quantity which is sufficient for being catalytically active for Fischer-Tropsch. The concentrations of cobalt can normally be at least 3% approximately, preferably from 5 to 45% by weight, more preferably from 10 to 30% by weight, referring to the total weight of the catalyst. The cobalt and possible promoters are dispersed in a carrier, for example silica, alumina or titanium oxide. The catalyst can contain other oxides, for example oxides of alkaline, earth-alkaline, rare-earth metals. The catalyst can also contain another metal which can be active as Fischer-Tropsch catalyst, for example a metal of groups 6 and 8 of the periodic table of elements, such as ruthenium, or which can be promoter, for example molybdenum, rhenium, hafnium, zirconium, cerium or uranium. The promoter metal(s) is usually present in a ratio, with respect to the cobalt, of at least 0.05:1, preferably at least 0.1:1, even more preferably from 0.1:1 to 1:1.

The above catalysts are generally in the form of fine powders usually having an average diameter of between 10 and 700 $\mu$m, preferably from 10 to 200 $\mu$m, even more preferably from 20 to 100 $\mu$m. The above catalysts are used in the presence of a liquid phase and a gas phase. In the case of Fischer-Tropsch synthesis, the liquid phase can consist of any inert liquid, for example one or more hydrocarbons having at least 5 carbon atoms per molecule. Preferably, the liquid phase essentially consists of saturated paraffins or olefinic polymers having a boiling point of more than 140° C. approximately, preferably higher than 280° C. approx. In addition appropriate liquid media can consist of paraffins produced by the Fischer-Tropsch reaction in the presence of any catalyst, preferably having a boiling point higher than 350° C. approx., preferably from 370 to 560° C.

The loading of the solids, or the volume of the catalyst with respect to the volume of suspension or diluent, can reach up to 50%, preferably from 5 to 40%.

In the case of Fischer-Tropsch, the feeding gas comprising carbon monoxide and hydrogen, can be diluted with other gases, more often up to a maximum of 30% by volume, preferably up to 20% by volume, usually selected from nitrogen, methane, carbon dioxide.

As far as the ratio between hydrogen and carbon monoxide is concerned, this can vary within a wide range. In the preferred embodiment, it is between 1:1 and 3:1, even more preferably from 1.2:1 to 2.5:1.

The regeneration treatment increases the activity of synthesis catalysts of hydrocarbons, reversibly and partially deactivated, independently of the procedure with which they have been prepared.

The following examples provide a better understanding of the present invention.

EXAMPLES

Example 1 describes the conditions required for the regeneration of the catalyst inside the bubble-column reactor with a draft-tube, without interrupting the hydrocarbons synthesis process, with a known geometry of the reactor and operating conditions at which the process takes place.

In example 1 an industrial reactor is used with a diameter of 10 m, having a draft-tube of 9.5 m in diameter, and the flow-rate of the gas containing hydrogen to be flushed into the base of the annular interspace, is calculated in relation to the flow-rate of the process gas. Three cases are studied in example 1: 0.2, 0.3, 0.4 m s$^{-1}$ as surface velocity of the process gas referring to the passage section of the draft-tube.

In example 2, the same conditions are maintained as in example 1, varying however, instead of the flow-rate of the process gas, the diameter of the draft-tube. The cases studied are 6.5, 8.5 and 9.5 m, whereas the surface velocity of the process gas, referring to the section of the draft-tube, remains constant and equal to 0.3 m s$^{-1}$. As in example 1, the flow-rate of the gas containing hydrogen, to be flushed into the base of the annular interspace, is calculated this time in relation to the diameter of the draft-tube.

Example 1

How to carry out the internal regeneration of the catalyst in a bubble-column reactor without interrupting the stream of process gas, with the synthesis of hydrocarbons in continuous.

I. Effect of the Flow-rate of the Process Gas

To ensure that the regeneration of the catalyst takes place without interrupting the Fischer-Tropsch synthesis, inside the bubble-column reactor equipped with a draft-tube, it is necessary to avoid that:

(a) the stream of gas containing hydrogen, which is introduced into the opening of the annular interspace, comes into contact with the process gas containing CO, which reacts with the hydrogen, as occurs in the synthesis process inside the draft-tube, preventing the regeneration of the catalyst;

(b) the liquid containing the solid in suspension circulates through the draft-tube and interspace, to be able to prevent mixing of the volume of slurry in which the reaction takes place and the volume of slurry in which the regeneration takes place, even if the stream of gas containing hydrogen is periodically interrupted to re-establish the forced circulation, due to the draft-tube, and to renew the loading (or volume) of slurry to be regenerated inside the annular interspace.

To satisfy the above items, in addition to suitable distribution systems of the process gas and gas containing hydrogen, the circulation of the liquid containing the catalyst in suspension must be minimized; to do this the hydrostatic head (which is the driving force of the liquid circulation) between the interspace and the draft-tube must tend towards zero:

$$\Delta P_H = (\epsilon_d - \epsilon_a)(\rho_{SL} - \rho_G)gH \quad (I)$$

wherein:
$\Delta P_H$=hydrostatic head between the interspace and the draft-tube, Pa;
$\epsilon_d$=gas holdup in the draft-tube;
$\epsilon_a$=gas holdup in the interspace;
$\rho_G$=density of the gaseous phase, kg m$^{-3}$;
$\rho_{SL}$=density of the slurry phase, kg m$^{-3}$;
g=gravity acceleration, m s$^{-2}$;
H=height of the free surface of the dispersion with respect to the bottom of the column, m.

In the balance (I) it is assumed that the average concentration of solid is the same in both the draft-tube and interspace, and also that the density of the process gas is comparable to that of the gas containing hydrogen for the regeneration of the catalyst.

In order to minimize the hydrostatic head, considering that the density of the slurry is at least an order of magnitude higher than that of the gas and that therefore their difference is always a finite value, there must be the same gas holdup in both the draft-tube and the interspace:

$$\epsilon_d = \epsilon_a \quad \text{(II)}$$

The above equation (II), when the reaction conditions, the geometry of the bubble-column reactor comprising the draft-tube and the flow-rate of process gas are established, can only be obtained with a specific flow-rate of gas containing hydrogen flushed into the interspace.

To describe the gas holdup in the draft-tube and interspace, a hydrodynamic model from literature was adopted (Krishna et al., A.I.Ch.E. Journal Vol. 43, 1997, pages 311–316) valid for a bubble-column in the presence of a gas-liquid-solid system with the slurry phase under "batch" conditions, which estimates the gas holdup in relation to the properties of the system, the diameter of the column and the superficial velocity of the gas. With respect to the annular region of the interspace, this was compared to a column with a diameter equal to the corresponding hydraulic diameter.

The hydrodynamic model from literature is applied by referring to a bubble-column reactor operating in the heterogeneous flow regime, which is typical of industrial-sized reactors, as is known to skilled person. The heterogeneous regime can be represented by means of a generalized two-phase model, in which one phase called "diluted" consists of the fraction of gas which flows through the reactor in the form of large bubbles. The second one ("dense" phase) can be represented by the liquid phase in which the particles of solid are suspended and the remaining fraction of gas in the form of small finely dispersed bubbles. The large bubbles, having a higher rise velocity than the small bubbles, can be essentially considered as being in plug flow. The dense phase, consisting of the liquid, suspended solid and small finely dispersed bubbles, has a certain degree of backmixing which depends on the operating conditions of the process and the diameter of the column. The hydrodynamic model from literature, which is based on a large number of experimental results, also assumes that the dependency of the gas holdup on the diameter of the column is valid up to a column diameter of 1 m, for higher diameters this influence being negligible. This can be explained by the fact that with a diameter of more than 1 m the bubbles of gas in the slurry bulk are no longer affected by the phenomenum known as "wall effect". Considering an industrial-sized bubble-column reactor, with a diameter of 10 m, in which the height of the slurry dispersion containing the gas is 30 m, inside of which is a draft-tube with a diameter of 9.5 m and a height of 29.8 m, situated at a distance of 10 cm above the bottom of the column in a co-axial position, the flow-rate of gas containing $H_2$ which satisfies balances (I) and (II), was examined in relation to the flow-rate of process gas to be adopted for the synthesis of hydrocarbons. The results, for the three cases in which the surface velocity of the process gas, referring to the section of the draft-tube, is equal to 0.2, 0.3 and 0.4 m/s, are indicated in table 1. In the above table, the gas holdup is also represented, which is the same, by definition, in the draft-tube and in the interspace when the catalyst is being regenerated. Table 2 on the other hand shows the flow-rates of liquid, containing the solid in suspension, which circulates through the interspace and draft-tube when the stream of gas containing hydrogen in the interspace, is interrupted, for the same cases described in table 1. These flow-rates of liquid were obtained by determining the actual velocity of the slurry (liquid with solid in suspension) in the draft-tube and interspace which satisfy the energy balance:

$$\Delta P_H = \Delta P_{LOSS} \quad \text{(III)}$$

where $\Delta P_H$ is the hydrostatic head between the interspace and the draft-tube, in Pa, whereas $\Delta P_{LOSS}$ refers to the total pressure drops of the bubble-column reactor with a draft-tube, which are obtained from the sum of the pressure drops by friction in the interspace, in the draft-tube and at the top and bottom of the draft-tube, where sudden section restrictions or enlargements and inversions of the slurry flow direction, take place.

The reaction conditions for all the cases are: 230° C. and 30 bars, the concentration of catalyst is 35% by volume, the density of the slurry 906 kg m$^{-3}$.

TABLE 1

| regeneration phase | | |
| --- | --- | --- |
| $U_d$ (m s$^{-1}$) | $\epsilon_d, \epsilon_a$ | $U_a$ (m s$^{-1}$) |
| 0.2 | 0.189 | 0.16 |
| 0.3 | 0.219 | 0.24 |
| 0.4 | 0.245 | 0.32 |

TABLE 2

| internal circulation phase of the slurry | |
| --- | --- |
| $U_d$ (m s$^{-1}$) | $Q_L$ (m$^3$ s$^{-1}$) |
| 0.2 | 17 |
| 0.3 | 19.5 |
| 0.4 | 21.5 |

Example 2

How to carry out the internal regeneration of the catalyst in a bubble-column reactor without interrupting the stream of process gas, with the synthesis of hydrocarbons in continuous.

II. Effect of the Diameter of the Draft-tube

In this example the same assumptions are maintained as for example 1, but instead of varying the superficial velocity of the process gas, the diameter of the draft-tube is varied. As in the previous example, the diameter of the industrial-sized column is 10 m, the height of the slurry dispersion containing the gas is 30 m, the height of the draft-tube is kept constant and is equal to 29.8 m, also the distance between the lower end of the draft-tube and the bottom of the column is assumed as being constant and equal to 10 cm. The surface velocity of the gas with respect to the free section of the passage of the draft-tube is set at 0.3 m s$^{-1}$, whereas the operating pressure and temperature of the synthesis process of hydrocarbons are, as in the previous example, 30 bars and 230° C.

The flow-rate of gas containing hydrogen which satisfies balances (I) and (II) of example 1 was examined in relation to the diameter of the draft-tube, $D_d$. The results, for three different diameter values of the draft-tube: 6.5, 8.5 and 9.5 m, are indicated in table 3, together with the area fraction occupied by the interspace with respect to the total area of the column (A %).

TABLE 3

| | regeneration phase | |
|---|---|---|
| $D_d$ (m) | A % | $U_a$ (m s$^{-1}$) |
| 6.5 | 58% | 0.3 |
| 8.5 | 28% | 0.3 |
| 9.5 | 10% | 0.24 |

As can be seen from the results of table 3, for the cases of a diameter of the draft-tube of 6.5 and 8.5 m, the superficial velocity which the gas containing hydrogen must have to satisfy balances (I) and (II) is the same as the process gas. The reason for this is that for both cases the hydraulic diameter relating to the interspace is greater than 1 m, therefore balance (II), for the assumptions indicated in example 1, proves to be independent of the diameter and depends exclusively on the gas velocity: as the correlations which describe the gas holdup in the interspace and the draft-tube are the same, balance (II) is only satisfied for the same gas-liquid-solid system when the superficial velocities of the two gases are the same.

When the stream of gas containing hydrogen is interrupted and the internal circulation of the liquid containing the solid in suspension is restarted, the flow-rates of circulating slurry which are obtained, for the same cases as table 3, are indicated in table 4.

TABLE 4

| internal circulation phase of the slurry | |
|---|---|
| $D_d$ (m) | $Q_L$ (m$^3$ s$^{-1}$) |
| 6.5 | 13.8 |
| 8.5 | 18 |
| 9.5 | 19.5 |

As can be observed from the data of table 4, the increase in diameter of the draft-tube increases the circulation of the slurry, similarly to what occurs when the flow-rate of the synthesis gas is increased maintaining the size of the draft-tube constant (see table 2).

TABLE 5

| effect of the diameter of the draft-tube on the circulation of the slurry | |
|---|---|
| $D_d$ (m) | $Q_L$ (m$^3$ s$^{-1}$) |
| 9.7 | 16.6 |
| 9.8 | 9.7 |
| 9.9 | 2.1 |
| 9.95 | 0.11 |

To maximize the reaction volume with respect to the regeneration volume, the section of the interspace must be reduced by increasing, with the same external diameter of the reactor, the diameter of the draft-tube.

However, if the diameter of the draft-tube is increased over a certain limit value, there is a sudden drop in the circulation flow-rate of the slurry (see table 5). This means that the draft effect induced by the presence of the draft-tube is diminished, whereas a certain amount of backmixing (undesired phenomenum) takes place inside the reaction volume. In table 5 it can be seen that, to have enough slurry recirculation, a draft-tube with a diameter less than 9.8 meters must be selected.

The conditions of table 5 are the same as table 4.

What is claimed is:

1. A continuous process for the production of a hydrocarbon, comprising:
   reacting a synthesis gas in the presence of a gas phase, a liquid and a solid catalyst using a bubble column equipped with cooling devices; and
   regenerating a reversibly, partially deactivated catalyst in the presence of a regenerating gas;
   wherein the bubble column comprises:
   (a) at least one draft tube, having a vertical cylinder and having smaller dimensions than the bubble column, with both a lower and an upper end open, completely immersed in the liquid phase containing the solid catalyst in suspension;
   (b) at least one device for an inlet for the synthesis gas;
   (c) at least one device for an inlet of the regenerating gas situated at a bottom of an interspace between the draft tube and an internal wall of the bubble column;
   (d) at least one device which activates or interrupts the stream of the regenerating gas; and
   (e) an optional device for minimizing a mixing of the synthesis gas with the regenerating gas.

2. The process according to claim 1, wherein the draft tube is positioned coaxially with respect to the bubble column.

3. The process according to claim 1, wherein the device (b) for the inlet of the synthesis gas is a gas distributor.

4. The process according to claim 1, wherein the device (b) for the inlet of the synthesis gas is situated at the bottom of the bubble column.

5. The process according to claim 1, wherein the device (c) for the inlet of the regenerating gas is a gas distributor.

6. The process according to claim 1, wherein the device (e) for minimizing the mixing of the synthesis gas with the regenerating gas is a deflector.

7. The process according to claim 1, wherein the device (e) for minimizing the mixing of the synthesis gas with the regenerating gas is assembled near the lower opening of the draft tube.

8. The process according to claim 1, wherein the lower end of the draft tube (a) is situated just above a bottom of the bubble column; and
   wherein the upper end of the draft tube (a) is situated just below a free surface of a solid-liquid suspension containing the solid catalyst.

9. The process according to claim 1, wherein the hydrocarbon is a heavy hydrocarbon, an alternative fuel, an octane enhancer, a chemical, a chemical intermediate, or mixtures thereof.

10. A process for regenerating a reversibly, partially deactivated solid catalyst, comprising:
    regenerating a quantity of said partially deactivated solid catalyst suspended in a liquid contained in an interspace between a bubble column and a draft tube without interrupting a flow of a synthesis gas by flushing a regeneration gas containing hydrogen into said interspace;
    balancing a hydrostatic head between said draft tube and said interspace by adjusting the flow rate of said regeneration gas;
    interrupting a feeding of said regeneration gas;
    reestablishing a circulation of said liquid containing said solid catalyst in suspension by means of said draft tube;
    thereby substituting a regenerated catalyst in said interspace for said partially deactivated solid catalyst from inside said draft tube;

wherein said bubble column comprises:
   (a) at least one draft tube, having a vertical cylinder and having smaller dimensions than said bubble column, with both a lower and an upper end open, completely immersed in said liquid containing a solid catalyst in suspension;
   (b) at least one device for an inlet for said synthesis gas;
   (c) at least one device for an inlet of said regeneration gas;
   (d) at least one device which activates or interrupts a stream of said regeneration gas; and
   (e) an optional device for minimizing a mixing of said synthesis gas with said regeneration gas.

11. The process according to claim 10, wherein during said regenerating said regeneration gas is flushed from a lower part of said interspace between said bubble column and said draft tube.

12. The process according to claim 10, wherein the process is repeated until there is a total regeneration of the catalyst in the bubble column.

13. A process according to claim 10, wherein the catalyst is selected from the group consisting of Group VIII metals.

14. A process according to claim 13, wherein the Group VIII metal is nickel or cobalt.

* * * * *